(12) United States Patent
Mano et al.

(10) Patent No.: US 9,260,700 B2
(45) Date of Patent: Feb. 16, 2016

(54) **BILIRUBIN OXIDASE FROM *MAGNAPORTHE ORYZAE* AND APPLICATIONS THEREOF**

(75) Inventors: Nicolas Mano, Talence (FR); Fabien Durand, Bordeaux (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/119,522

(22) PCT Filed: May 22, 2012

(86) PCT No.: PCT/IB2012/052570
§ 371 (c)(1),
(2), (4) Date: Jan. 2, 2014

(87) PCT Pub. No.: WO2012/160517
PCT Pub. Date: Nov. 29, 2012

(65) Prior Publication Data
US 2014/0120566 A1 May 1, 2014

(30) Foreign Application Priority Data
May 24, 2011 (FR) .................................. 11 54526

(51) Int. Cl.
*C12N 9/02* (2006.01)
*C12Q 1/00* (2006.01)
*C02F 3/34* (2006.01)
*C12Q 1/26* (2006.01)
*G01N 33/72* (2006.01)
*H01M 8/16* (2006.01)

(52) U.S. Cl.
CPC ................ *C12N 9/001* (2013.01); *C02F 3/342* (2013.01); *C12Q 1/005* (2013.01); *C12Q 1/26* (2013.01); *C12Y 103/03005* (2013.01); *G01N 33/723* (2013.01); *G01N 33/728* (2013.01); *H01M 8/16* (2013.01); *Y02E 60/527* (2013.01)

(58) Field of Classification Search
None
See application file for complete search history.

(56) References Cited

U.S. PATENT DOCUMENTS

| 4,600,689 | A | 7/1986 | Matsui et al. |
|---|---|---|---|
| 4,677,062 | A | 6/1987 | Uwajima et al. |
| 4,701,411 | A | 10/1987 | Wu |
| 4,746,606 | A | 5/1988 | Wu |
| 4,770,997 | A | 9/1988 | Yoshino et al. |
| 4,985,360 | A | 1/1991 | Takahashi et al. |
| 5,624,811 | A | 4/1997 | Lang et al. |
| 6,152,967 | A | 11/2000 | Maubru |
| 6,610,172 | B1 | 8/2003 | Lund et al. |
| 2002/0017992 | A1 | 2/2002 | Hidaka et al. |
| 2008/0169206 | A1 | 7/2008 | Pei et al. |
| 2009/0053582 | A1 | 2/2009 | Sugiyama et al. |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report for PCT/IB2012/052570 dated Sep. 3, 2012.
Written Opinion of the International Searching Authority for PCT/IB2012/052570 dated Sep. 3, 2012.
Database UniProt [Online], (May 15, 2007), XP002680879, retrieved from EBI accession No. A4QV27, Database accession No. A4QV27, cited in the application, the whole document.
Kataoka K et al: "High-level expression of Myrothecium verrucaria bilirubin oxidase in Pichia pastoris, and its facile purification and characterization", Protein Expression and Purification, Academic Press, San Diego, CA, vol. 41, No. 1, (May 1, 2005), pp. 77-83.
Liu Y et al: "Decolorization and biodegradation of remazol brilliant blue R by bilirubin oxidase", Journal of Bioscience and Bioengineering, Elsevier, Amsterdam, NL, vol. 108, No. 6, (Dec. 1, 2009), pp. 496-500.
Shleev S et al: "Direct electron transfer between copper-containing proteins and electrodes", Biosensors and Bioelectronics, Elsevier BV, NL, vol. 20, No. 12, (Jun. 15, 2005) pp. 2517-2554.
Fabien Durand et al: "Bilirubin oxidase from Magnaporthe oryzae: an attractive new enzyme for biotechnological applications", Applied Microbiology and Biotechnology, (Feb. 15, 2012).

* cited by examiner

*Primary Examiner* — Christian Fronda
(74) *Attorney, Agent, or Firm* — B. Aaron Schulman, Esq.; Stites & Harbison, PLLC

(57) ABSTRACT

The present invention relates to a novel bilirubin oxidase from *Magnaporthe oryzae*, to the method of preparation thereof as well as use thereof notably for assay of bilirubin and for the application of enzymatic biofuel cells.

5 Claims, 6 Drawing Sheets

SEQUENCE LISTING

```
<160> NUMBER OF SEQ ID NOS: 7

<210> SEQ ID NO 1
<211> LENGTH: 570
<212> TYPE: PRT
<213> ORGANISM: Magnaporthe oryzae

<400> SEQUENCE: 1

Lys Asp Trp Ile Ser Pro Leu Tyr Pro Leu Ile Phe Lys Thr Pro Leu
```

```
1               5                   10                  15
Pro Ile Pro Pro Ile Lys Glu Pro Leu Lys Lys Leu Lys Asn Gln Ile
                20                  25                  30
Ser Gly Gly Asp Ile Trp Tyr Tyr Glu Met Asp Ile Lys Pro Tyr Ser
            35                  40                  45
Gln Gln Val Tyr Thr Asp Arg Gly Ala Ala His Leu Val Gly Tyr Asp
        50                  55                  60
Gly Val Ser Pro Gly Pro Thr Ile Ile Val Pro Arg Gly Val Glu Thr
65                  70                  75                  80
Val Val Arg Phe Val Asn Asn Ala Ala Leu Pro Asn Ser Val His Leu
                85                  90                  95
His Gly Ser Tyr Ser Arg Ala Pro Phe Asp Gly Trp Ala Glu Asp Val
            100                 105                 110
Thr Asn Pro Gly Glu Phe Lys Asp Tyr Tyr Pro Asn Gln Gln Ser
        115                 120                 125
Ala Arg Met Leu Trp Tyr His Asp His Ala Val His Ile Thr Ala Glu
    130                 135                 140
Asn Ala Tyr Met Gly Gln Ala Gly Ala Tyr Ile Ile Thr Asp Pro Ala
145                 150                 155                 160
Glu Asp Ala Leu Asn Leu Pro Ala Gly Tyr Gly Lys Tyr Asp Ile Pro
                165                 170                 175
Leu Val Leu Thr Ala Lys Ser Tyr Gln Glu Asn Gly Asp Leu Val Ser
            180                 185                 190
Thr Asn Gly Glu Glu Asp Ser Phe Trp Gly Asp Val Ile His Val Asn
        195                 200                 205
Gly Gln Pro Trp Pro Phe Leu Asn Val Glu Pro Arg Lys Tyr Arg Phe
    210                 215                 220
Arg Phe Leu Asp Ala Ala Val Ser Arg Ser Phe Ala Leu Tyr Phe Ser
225                 230                 235                 240
Pro Val Gly Ser Ser Ala Lys Ile Pro Phe Gln Val Ile Ala Ser
                245                 250                 255
Asp Ala Gly Leu Leu Glu Ser Pro Gln Gln Val Ser Asn Ile Phe Leu
            260                 265                 270
Ala Asn Ala Glu Arg Tyr Glu Val Val Phe Asp Phe Ser Gln Tyr Ala
        275                 280                 285
Gly Gln Ala Ile Asp Leu Leu Asn Leu Pro Gly Ala Gly Gly Pro Gly
    290                 295                 300
Val Glu Lys Asp Tyr Ser Asn Thr Asp Lys Val Met Arg Phe Ile Val
305                 310                 315                 320
Gly Asp Lys Val Ala Ala Pro Asp Thr Ser Val Val Pro Ser Ala Leu
                325                 330                 335
Arg Thr Val Pro Phe Pro Lys Pro Val Thr Asn Asn Ala Ile Ser His
            340                 345                 350
Phe Phe Arg Phe His Arg Gln Lys Ser Glu Trp Arg Ile Asn Gly Ile
        355                 360                 365
Thr Phe Ala Asp Val Asn Asn Arg Met Leu Ala Asn Val Pro Arg Gly
    370                 375                 380
Thr Val Glu Ile Trp Glu Leu Glu Asn Ser Ser Gly Gly Trp Ser His
385                 390                 395                 400
Pro Ile His Ile His Leu Ile Asp Phe Arg Val Leu Ala Arg Asp Gly
                405                 410                 415
Pro Arg Ser Val Met Pro Tyr Glu Ala Ala Gly Leu Lys Asp Val Val
            420                 425                 430
```

-continued

```
Trp Leu Gly Arg Asn Glu Lys Val Leu Val Glu Ala His Tyr Ala Pro
        435                 440                 445

Trp Asp Gly Val Tyr Met Phe His Cys His Asn Leu Ile His Glu Asp
    450                 455                 460

His Asp Met Met Ala Ala Phe Asn Val Thr Ala Leu Pro Asp Phe Gly
465                 470                 475                 480

Tyr Asp Glu Lys Thr His Phe Ile Asp Pro Met Glu Gln Arg Trp Arg
                485                 490                 495

Ala Lys Pro Phe Gly Ala Ala Asp Phe Lys Ala Arg Thr Gly Ala Phe
            500                 505                 510

Ser Asp Ala Asn Ile Glu Ala Ala Val Ala Phe Leu Ala Asp Thr Asp
        515                 520                 525

Ala Tyr Ser Lys Val Asp Ile Val Asn Gln Asn Leu Asp Ser Tyr Trp
    530                 535                 540

Ala Ala Lys Gly Leu Lys Ala Arg Lys Val Gly Glu Arg Gln Ala Glu
545                 550                 555                 560

Gly Pro Ile Pro Arg Tyr Met Pro Arg Gln
                565                 570

<210> SEQ ID NO 2
<211> LENGTH: 1785
<212> TYPE: DNA
<213> ORGANISM: Magnaporthe oryzae

<400> SEQUENCE: 2
atgccagagg ccgagaggat cgccctctcg caagtcgtcg aggatgaccc caacgacatc      60
accgacccgg caaaggactg gatcagcccc ctgtacccct tgatcttcaa gacccccctg     120
cccatccctc ccatcaagga gcctctcaag aagctcaaga accagatcag cggtggcgac     180
atttggtact atgagatgga catcaagccc tactcccagc aggtctacac cgaccgtgga     240
gctgcccacc ttgtcggcta cgacggtgta tcccctggac ccaccatcat cgttccccgt     300
ggcgttgaga ccgttgttcg attcgtcaac aacgctgctc tccccaactc ggtccacctt     360
cacggttcat actcgcgtgc cccctttgac ggctgggctg aggacgtcac caaccccggc     420
gagttcaagg actactacta ccccaaccag cagtccgccc gcatgctctg gtaccacgac     480
cacgccgtcc acatcacggc cgagaacgcc tacatgggac aggccggcgc ctacatcatc     540
acggaccccg ccgaggacgc cctcaacctc cccgcgggct acggcaagta cgacatcccg     600
ctggtcctga ccgccaagtc gtaccaggag aacggcgacc tggtctcgac caacggcgag     660
gaggacagct tctggggcga cgtgatccac gtcaacggcc agccctggcc cttcttgaac     720
gtcgagccgc gcaagtaccg cttccgcttc ctcgacgccg ccgtctcgcg ctcctttgcc     780
ctgtacttta gccccgtcgg ctccagcagc gccaagatcc ccttccaggt catcgcgtcc     840
gacgccggcc tgctcgagtc cccccagcag gtctccaaca tcttcctggc caacgccgag     900
cgctacgagg tcgtctttga cttttcccag tacgccggcc aggccatcga cctgctgaac     960
cttcccggcg ccggcggccc cggtgtcgaa aaggactact ccaacaccga caaggtcatg    1020
cgcttcatcg tgggcgacaa ggtcgccgcc cccgacacca gcgtcgtccc ctctgctctg    1080
cgcaccgtcc ccttccccaa gcccgtgacc aacaacgcca tcagccactt cttccgcttc    1140
caccgccaaa agtccgagtg gcgcatcaac ggcatcacct ttgccgacgt caacaaccgc    1200
atgctcgcca acgtcccccg cggaaccgtc gagatctggg agctcgagaa ctcgtccggc    1260
ggctggtccc accccatcca catccacctg atcgacttta gggtgctggc tcgcgatggt    1320
```

```
ccccgctccg tcatgcccta cgaggccgcc ggtctcaagg acgtcgtctg gctgggccgc   1380
aacgaaaagg tcctggtcga ggcccactac gcccccctggg acggcgttta catgttccac   1440
tgccacaacc tgatccacga ggaccacgac atgatggccg ccttcaacgt gaccgccctg   1500
cccgactttg gctacgatga aaagactcac ttcatcgacc ccatggagca gcgctggcgt   1560
gccaagccgt tcggtgctgc cgatttcaag gctcgcactg gtgcctttag cgatgccaac   1620
atcgaggctg ccgttgcctt cctggcagac accgatgcct acagcaaggt cgacattgtg   1680
aaccagaacc tcgacagcta ctgggctgcc aagggtctca aggctcgcaa ggttggcgag   1740
aggcaggccg agggacccat cccccgctac atgccgcgtc agtga                     1785

<210> SEQ ID NO 3
<211> LENGTH: 571
<212> TYPE: PRT
<213> ORGANISM: Magnaporthe oryzae

<400> SEQUENCE: 3

Ser Lys Asp Trp Ile Ser Pro Leu Tyr Pro Leu Ile Phe Lys Thr Pro
1               5                   10                  15

Leu Pro Ile Pro Pro Ile Lys Glu Pro Leu Lys Lys Leu Lys Asn Gln
            20                  25                  30

Ile Ser Gly Gly Asp Ile Trp Tyr Tyr Glu Met Asp Ile Lys Pro Tyr
        35                  40                  45

Ser Gln Gln Val Tyr Thr Asp Arg Gly Ala Ala His Leu Val Gly Tyr
    50                  55                  60

Asp Gly Val Ser Pro Gly Pro Thr Ile Ile Val Pro Arg Gly Val Glu
65                  70                  75                  80

Thr Val Val Arg Phe Val Asn Asn Ala Ala Leu Pro Asn Ser Val His
                85                  90                  95

Leu His Gly Ser Tyr Ser Arg Ala Pro Phe Asp Gly Trp Ala Glu Asp
            100                 105                 110

Val Thr Asn Pro Gly Glu Phe Lys Asp Tyr Tyr Tyr Pro Asn Gln Gln
        115                 120                 125

Ser Ala Arg Met Leu Trp Tyr His Asp His Ala Val His Ile Thr Ala
    130                 135                 140

Glu Asn Ala Tyr Met Gly Gln Ala Gly Ala Tyr Ile Ile Thr Asp Pro
145                 150                 155                 160

Ala Glu Asp Ala Leu Asn Leu Pro Ala Gly Tyr Gly Lys Tyr Asp Ile
                165                 170                 175

Pro Leu Val Leu Thr Ala Lys Ser Tyr Gln Glu Asn Gly Asp Leu Val
            180                 185                 190

Ser Thr Asn Gly Glu Glu Asp Ser Phe Trp Gly Asp Val Ile His Val
        195                 200                 205

Asn Gly Gln Pro Trp Pro Phe Leu Asn Val Glu Pro Arg Lys Tyr Arg
    210                 215                 220

Phe Arg Phe Leu Asp Ala Ala Val Ser Arg Ser Phe Ala Leu Tyr Phe
225                 230                 235                 240

Ser Pro Val Gly Ser Ser Ser Ala Lys Ile Pro Phe Gln Val Ile Ala
                245                 250                 255

Ser Asp Ala Gly Leu Leu Glu Ser Pro Gln Gln Val Ser Asn Ile Phe
            260                 265                 270

Leu Ala Asn Ala Glu Arg Tyr Glu Val Val Phe Asp Phe Ser Gln Tyr
        275                 280                 285
```

-continued

```
Ala Gly Gln Ala Ile Asp Leu Leu Asn Leu Pro Gly Ala Gly Gly Pro
    290                 295                 300

Gly Val Glu Lys Asp Tyr Ser Asn Thr Asp Lys Val Met Arg Phe Ile
305                 310                 315                 320
Val Gly Asp Lys Val Ala Ala Pro Asp Thr Ser Val Val Pro Ser Ala
                325                 330                 335
Leu Arg Thr Val Pro Phe Pro Lys Pro Val Thr Asn Asn Ala Ile Ser
            340                 345                 350
His Phe Phe Arg Phe His Arg Gln Lys Ser Glu Trp Arg Ile Asn Gly
        355                 360                 365
Ile Thr Phe Ala Asp Val Asn Asn Arg Met Leu Ala Asn Val Pro Arg
    370                 375                 380
Gly Thr Val Glu Ile Trp Glu Leu Glu Asn Ser Ser Gly Gly Trp Ser
385                 390                 395                 400
His Pro Ile His Ile His Leu Ile Asp Phe Arg Val Leu Ala Arg Asp
                405                 410                 415
Gly Pro Arg Ser Val Met Pro Tyr Glu Ala Ala Gly Leu Lys Asp Val
            420                 425                 430
Val Trp Leu Gly Arg Asn Glu Lys Val Leu Val Glu Ala His Tyr Ala
        435                 440                 445
Pro Trp Asp Gly Val Tyr Met Phe His Cys His Asn Leu Ile His Glu
    450                 455                 460
Asp His Asp Met Met Ala Ala Phe Asn Val Thr Ala Leu Pro Asp Phe
465                 470                 475                 480
Gly Tyr Asp Glu Lys Thr His Phe Ile Asp Pro Met Glu Gln Arg Trp
                485                 490                 495
Arg Ala Lys Pro Phe Gly Ala Ala Asp Phe Lys Ala Arg Thr Gly Ala
            500                 505                 510
Phe Ser Asp Ala Asn Ile Glu Ala Ala Val Ala Phe Leu Ala Asp Thr
        515                 520                 525
Asp Ala Tyr Ser Lys Val Asp Ile Val Asn Gln Asn Leu Asp Ser Tyr
    530                 535                 540
Trp Ala Ala Lys Gly Leu Lys Ala Arg Lys Val Gly Glu Arg Gln Ala
545                 550                 555                 560
Glu Gly Pro Ile Pro Arg Tyr Met Pro Arg Gln
                565                 570
```

<210> SEQ ID NO 4
<211> LENGTH: 1716
<212> TYPE: DNA
<213> ORGANISM: Magnaporthe oryzae

<400> SEQUENCE: 4

```
agcaaggact ggatcagccc cctgtacccc ttgatcttca agaccccccct gcccatccct     60 cccatcaagg agcctctcaa gaagctcaag aaccagatca gcggtggcga catttggtac    120
tatgagatgg acatcaagcc ctactcccag caggtctaca ccgaccgtgg agctgcccac    180
cttgtcggct acgacggtgt atcccctgga cccaccatca tcgttccccg tggcgttgag    240
accgttgttc gattcgtcaa caacgctgct ctccccaact cggtccacct tcacggttca    300
tactcgcgtg cccccttga cggctgggct gaggacgtca ccaaccccgg cgagttcaag    360
gactactact accccaacca gcagtccgcc cgcatgctct ggtaccacga ccacgccgtc    420
cacatcacgg ccgagaacgc ctacatggga caggccggcg cctacatcat cacggacccc    480
gccgaggacg ccctcaacct ccccgcgggc tacggcaagt acgacatccc gctggtcctg    540
```

-continued

```
accgccaagt cgtaccagga gaacggcgac ctggtctcga ccaacggcga ggaggacagc    600
ttctggggcg acgtgatcca cgtcaacggc cagccctggc ccttcttgaa cgtcgagccg    660
cgcaagtacc gcttccgctt cctcgacgcc gccgtctcgc gctcctttgc cctgtacttt    720
agccccgtcg gctccagcag cgccaagatc cccttccagg tcatcgcgtc cgacgccggc    780
ctgctcgagt ccccccagca ggtctccaac atcttcctgg ccaacgccga gcgctacgag    840
gtcgtctttg acttttccca gtacgccggc caggccatcg acctgctgaa ccttcccggc    900
gccggcggcc ccggtgtcga aaaggactac tccaacaccg acaaggtcat gcgcttcatc    960
gtgggcgaca aggtcgccgc ccccgacacc agcgtcgtcc cctctgctct gcgcaccgtc   1020
cccttcccca agcccgtgac caacaacgcc atcagccact tcttccgctt ccaccgccaa   1080
aagtccgagt ggcgcatcaa cggcatcacc tttgccgacg tcaacaaccg catgctcgcc   1140
aacgtccccc gcggaaccgt cgagatctgg gagctcgaga actcgtccgg cggctggtcc   1200
caccccatcc acatccacct gatcgacttt agggtgctgg ctcgcgatgg tccccgctcc   1260
gtcatgccct acgaggccgc cggtctcaag gacgtcgtct ggctgggccg caacgaaaag   1320
gtcctggtcg aggcccacta cgccccctgg gacggcgttt acatgttcca ctgccacaac   1380
ctgatccacg aggaccacga catgatggcc gccttcaacg tgaccgccct gcccgacttt   1440
ggctacgatg aaaagactca cttcatcgac cccatggagc agcgctggcg tgccaagccg   1500
ttcggtgctg ccgatttcaa ggctcgcact ggtgccttta gcgatgccaa catcgaggct   1560
gccgttgcct tcctggcaga caccgatgcc tacagcaagg tcgacattgt gaaccagaac   1620
ctcgacagct actgggctgc caagggtctc aaggctcgca aggttggcga gaggcaggcc   1680
gagggaccca tcccccgcta catgccgcgt cagtga                             1716
```

<210> SEQ ID NO 5
<211> LENGTH: 594
<212> TYPE: PRT
<213> ORGANISM: Magnaporthe oryzae

<400> SEQUENCE: 5

```
Met Pro Glu Ala Glu Arg Ile Ala Leu Ser Gln Val Val Glu Asp Asp
1               5                   10                  15

Pro Asn Asp Ile Thr Asp Pro Ala Lys Asp Trp Ile Ser Pro Leu Tyr
            20                  25                  30

Pro Leu Ile Phe Lys Thr Pro Leu Pro Ile Pro Pro Ile Lys Glu Pro
        35                  40                  45

Leu Lys Lys Leu Lys Asn Gln Ile Ser Gly Gly Asp Ile Trp Tyr Tyr
    50                  55                  60

Glu Met Asp Ile Lys Pro Tyr Ser Gln Gln Val Tyr Thr Asp Arg Gly
65                  70                  75                  80

Ala Ala His Leu Val Gly Tyr Asp Gly Val Ser Pro Gly Pro Thr Ile
                85                  90                  95

Ile Val Pro Arg Gly Val Glu Thr Val Val Arg Phe Val Asn Asn Ala
            100                 105                 110

Ala Leu Pro Asn Ser Val His Leu His Gly Ser Tyr Ser Arg Ala Pro
        115                 120                 125

Phe Asp Gly Trp Ala Glu Asp Val Thr Asn Pro Gly Glu Phe Lys Asp
    130                 135                 140

Tyr Tyr Tyr Pro Asn Gln Gln Ser Ala Arg Met Leu Trp Tyr His Asp
145                 150                 155                 160
```

-continued

```
His Ala Val His Ile Thr Ala Glu Asn Ala Tyr Met Gly Gln Ala Gly
                165                 170                 175

Ala Tyr Ile Ile Thr Asp Pro Ala Glu Asp Ala Leu Asn Leu Pro Ala
            180                 185                 190

Gly Tyr Gly Lys Tyr Asp Ile Pro Leu Val Leu Thr Ala Lys Ser Tyr
        195                 200                 205

Gln Glu Asn Gly Asp Leu Val Ser Thr Asn Gly Glu Asp Ser Phe
    210                 215                 220

Trp Gly Asp Val Ile His Val Asn Gly Gln Pro Trp Pro Phe Leu Asn
225                 230                 235                 240

Val Glu Pro Arg Lys Tyr Arg Phe Arg Phe Leu Asp Ala Ala Val Ser
                245                 250                 255

Arg Ser Phe Ala Leu Tyr Phe Ser Pro Val Gly Ser Ser Ala Lys
            260                 265                 270

Ile Pro Phe Gln Val Ile Ala Ser Asp Ala Gly Leu Leu Glu Ser Pro
        275                 280                 285

Gln Gln Val Ser Asn Ile Phe Leu Ala Asn Ala Glu Arg Tyr Glu Val
    290                 295                 300

Val Phe Asp Phe Ser Gln Tyr Ala Gly Gln Ala Ile Asp Leu Leu Asn
305                 310                 315                 320

Leu Pro Gly Ala Gly Gly Pro Gly Val Glu Lys Asp Tyr Ser Asn Thr
                325                 330                 335

Asp Lys Val Met Arg Phe Ile Val Gly Asp Lys Val Ala Ala Pro Asp
            340                 345                 350

Thr Ser Val Val Pro Ser Ala Leu Arg Thr Val Pro Phe Pro Lys Pro
        355                 360                 365

Val Thr Asn Asn Ala Ile Ser His Phe Phe Arg Phe His Arg Gln Lys
    370                 375                 380

Ser Glu Trp Arg Ile Asn Gly Ile Thr Phe Ala Asp Val Asn Asn Arg
385                 390                 395                 400

Met Leu Ala Asn Val Pro Arg Gly Thr Val Glu Ile Trp Glu Leu Glu
                405                 410                 415

Asn Ser Ser Gly Gly Trp Ser His Pro Ile His Ile His Leu Ile Asp
            420                 425                 430

Phe Arg Val Leu Ala Arg Asp Gly Pro Arg Ser Val Met Pro Tyr Glu
        435                 440                 445

Ala Ala Gly Leu Lys Asp Val Val Trp Leu Gly Arg Asn Glu Lys Val
    450                 455                 460

Leu Val Glu Ala His Tyr Ala Pro Trp Asp Gly Val Tyr Met Phe His
465                 470                 475                 480

Cys His Asn Leu Ile His Glu Asp His Asp Met Met Ala Ala Phe Asn
                485                 490                 495

Val Thr Ala Leu Pro Asp Phe Gly Tyr Asp Glu Lys Thr His Phe Ile
            500                 505                 510

Asp Pro Met Glu Gln Arg Trp Arg Ala Lys Pro Phe Gly Ala Ala Asp
        515                 520                 525

Phe Lys Ala Arg Thr Gly Ala Phe Ser Asp Ala Asn Ile Glu Ala Ala
    530                 535                 540

Val Ala Phe Leu Ala Asp Thr Asp Ala Tyr Ser Lys Val Asp Ile Val
545                 550                 555                 560

Asn Gln Asn Leu Asp Ser Tyr Trp Ala Ala Lys Gly Leu Lys Ala Arg
                565                 570                 575

Lys Val Gly Glu Arg Gln Ala Glu Gly Pro Ile Pro Arg Tyr Met Pro
```

Arg Gln

```
<210> SEQ ID NO 6
<211> LENGTH: 6
<212> TYPE: DNA
<213> ORGANISM: artificial
<220> FEATURE:
<223> OTHER INFORMATION: oligonucleotide

<400> SEQUENCE: 6 gctagc                                                                  6

<210> SEQ ID NO 7
<211> LENGTH: 8
<212> TYPE: DNA
<213> ORGANISM: artificial
<220> FEATURE:
<223> OTHER INFORMATION: oligonucleotide

<400> SEQUENCE: 7 gcggccgc                                                                8
```

BILIRUBIN OXIDASE FROM *MAGNAPORTHE ORYZAE* AND APPLICATIONS THEREOF

The present invention relates to a novel bilirubin oxidase, the method of preparation thereof as well as use thereof notably for determination of bilirubin and for the application of enzymatic biofuel cells using oxygen as fuel.

Bilirubin oxidase or BOD (E.C. 1.3.3.5) is an enzyme that catalyses the reaction of oxidation of bilirubin to biliverdin;

$$\text{bilirubin} + \tfrac{1}{2} O_2 \rightarrow \text{biliverdin} + H_2O$$

BOD has four binding sites with copper atoms; these four copper atoms are necessary for the proper activity of the enzyme, and it has in fact been shown that the absence of one copper from the protein CotA of *Bacillus subtilis* (a protein with bilirubin oxidase activity marketed, as BOD, by the company Genzyme Diagnostics) was sufficient to reduce the activity of the enzyme (Table 3 of the article by Durao et al. in J Biol Inorg Chem. 2008 Febuary; 13(2):183-93). It should be noted that the presence, in the sequence of an enzyme, of binding sites with four copper ions such as those present in BOD does not enable us to deduce its enzymatic activity; in fact, there are various enzymes that share the characteristic of possessing such sites (such as laccases for example).

Bilirubin is a yellow substance formed in the blood by decomposition of haemoglobin, and is one of the main pigments produced in the liver.

BOD is of interest for various applications such as determination of bilirubin, making it possible for example to diagnose excess bilirubin in the blood; it can also be used for preparing enzymatic biofuel cells, in which it will capture the electrons from the cathode, reducing oxygen to water (see the schematic representation of an enzymatic biofuel cell, where BOD is fixed in a redox polymer at the cathode in FIG. 1A) or as an oxygen biosensor.

There are numerous sources of BOD; this enzyme can be produced by microorganisms such as those of the genus *Bacillus* [*Bacillus subtilis* whose CotA has bilirubin oxidase activity, see Sakasegawa et al. 2006 Applied and Environmental Microbiology 72, No. 1, 972-975; *Bacillus licheniformis* (U.S. Pat. No. 4,770,997)], or by mycetes, among them those of the genus *Penicillium* [*Penicillium janthinellum* (Patent application EP 0 295 101)], *Trachyderma* (U.S. Pat. No. 4,600,689), *Myrothecium* (Tanaka et al. 1982 Agric. Biol. Chem. 46, 2499-2503) or *Schizophyllum, Coprinus, Trametes, Coriolus, Pholiota, Pleurotus, Lenzites* or *Fomitopsis* (U.S. Pat. No. 4,677,062).

This enzyme can also be extracted from plants such as of the genus *Alfalfa* (U.S. Pat. No. 5,624,811), Solanaceae, Musaceae and Liliaceae (EP 0 140 004) or Compositae such as artichoke (EP 0 247 846).

Among these enzymes, the BODs displaying the most advantageous enzymatic properties, in particular activity and stability, have been adopted for commercialization; these are CotA with bilirubin oxidase activity from *Bacillus subtilis* (it is sold as BOD by the company Genzyme Diagnostics and will be designated BOD hereinafter) and BOD from *Myrothecium verrucaria* (sold by the companies Sigma-Aldrich and Amano).

The inventors have now identified a new BOD produced by *Magnaporthe oryzae* which is much more active at acid pH (below 5) and, in particular, at temperature below 50° C. than the commercially available BODs.

According to a first object, the invention relates to the BOD from *Magnaporthe oryzae* of SEQ. ID. No.1; this enzyme corresponds to a predicted protein deduced from sequencing of the genome of *Magnaporthe oryzae* (translated on the basis of the gene having accession number A4QV27 in the Uniprot database, this complete gene has the sequence SEQ. ID. No.2) except for the 24 amino acids positioned at the N-terminal end of the protein; in particular, the purified bilirubin oxidase (purity>95%) according to the invention has a percentage identity of at least 80%, and in order of increasing preference at least 85%, 90%, 95%, 97%, 98% and 99% of identity, relative to the BOD from *Magnaporthe oryzae* of SEQ. ID. No.1; it catalyses the reaction of oxidation of bilirubin to biliverdin and is bound to four copper atoms. The nucleic acid sequence SEQ. ID. No.4 (corresponding to SEQ. ID. No.2 excluding the fragment coding for the 24 amino acids positioned at the N-terminal end) codes for this BOD of SEQ. ID. No.1.

The BOD of SEQ. ID. No.3 is also an object of the present invention; the BOD of SEQ. ID. No.3 differs from the BOD of SEQ. ID. No.1 in that it comprises an additional amino acid, a serine, in N-terminal position; this BOD is obtained by expressing, in the yeast *Pichia pastoris*, the nucleic acid molecule of SEQ. ID. No.4 cloned into the pFD55 expression vector, whose construction is such that it permits the expression of a protein bearing an additional serine in N-terminal position.

The BOD of SEQ. ID. No.5, which corresponds to the polypeptide encoded by SEQ. ID. No.2 and which comprises the 24 amino acids of the N-terminal end, is also an object of the present invention.

In general, the inventors found that the sequence modifications introduced at the N-terminal end, whether it is addition of amino acids or substitution, deletion or insertion within the N-terminal end, in the limit maintaining an identity of at least 80%, preferably 90%, with SEQ. ID. No.1, did not affect the enzymatic properties of the BOD according to the invention.

The identity of a sequence relative to the sequence of the BOD from *Magnaporthe oryzae* (SEQ. ID. No.1) as reference sequence is assessed in relation to the percentage of amino acid residues that are identical, when the two sequences are aligned, so as to obtain the maximum correspondence between them.

The percentage identity can be calculated by a person skilled in the art using sequence comparison software, for example the BLAST suite (Altschul et al., NAR, 25, 3389-3402). The BLAST programs are applied on the comparison window consisting of the whole of SEQ. ID. No.2 indicated as reference sequence.

A peptide having an amino acid sequence having at least X % of identity with a reference sequence is defined, in the present invention, as a peptide whose sequence can include up to 100-X alterations for 100 amino acids of the reference sequence, while conserving the functional properties of said reference peptide, in this case its enzymatic activity of bilirubin oxidation. In the sense of the present invention, the term alteration includes consecutive or dispersed deletions, substitutions or insertions of amino acids in the reference sequence.

A protein sequence SEQ. ID. No.5 predicted from systematic sequencing of the genome of *Magnaporthe oryzae* is described in the Uniprot database (accession number A4QV27); it should be emphasized that the information presented in the Uniprot database is predictive and putative, it does not result from isolation and experimental characterization of proteins of *Magnaporthe oryzae*. Moreover, for this predicted protein, the Uniprot database does not indicate any particular enzymatic activity.

The novel BOD according to the invention has improved properties relative to the commercially available BODs derived from *Myrothecium verrucaria* or from *Bacillus subtilis*.

In particular, the BOD from *Magnaporthe oryzae* displays enzymatic properties (activity, catalytic efficiency $k_{cat}$ and affinity of the substrate for the enzyme $K_M$) of catalysis of the oxidation of certain substrates superior to the BOD from *Bacillus subtilis* (see the experimental section given below).

The following Table I shows the catalytic efficiency $k_{cat}$, i.e. the number of molecules of substrate converted to product per molecule of enzyme and per unit time, and the Michaelis constant $K_M$, which represents the affinity of the substrate (ABTS) for the BODs from *B. subtilis* and from *Magnaporthe oryzae*.

TABLE I enzymatic properties of the BODs from *M. oryzae* and *B. subtilis*

| BOD | $k_{cat}$ (for ABTS) | $K_M$ |
|---|---|---|
| *Magnaporthe oryzae* | 668 s$^{-1}$ | 42.8 μM |
| *B. subtilis* | 322 s$^{-1}$ | 124 μM |

The enzymatic properties described for the BOD from *M. verrucaria* by Kataoka et al. (2005, Protein Expression and Purification, 41, 77-83) at pH 6.5 are a $k_{cat}$ of 115 s$^{-1}$ and a $K_M$ of 250 μM. Moreover, the BOD from *Magnaporthe oryzae* also displays good enzymatic properties of oxidation of bilirubin.

The present invention also relates to a nucleic acid molecule coding for the BOD according to the invention; preferably, it is a nucleic acid molecule of sequence selected from SEQ. ID. No.2 or 4, preferably it is SEQ. ID. No.4 coding for the BOD from *Magnaporthe oryzae* cleaved at the level of the first 24 amino acids positioned at the N-terminal end of the protein.

The nucleic acid molecule coding for the BOD according to the invention can be cloned into an expression vector such as a plasmid, then transformed into a suitable host such as a bacterium, a yeast or a cell culture.

"Expression vector" means a vector possessing a region permitting the insertion of a coding nucleotide sequence between the signals indispensable for its expression, notably, a promoter (constitutive or inducible), a ribosome attachment site, a transcription termination signal and, optionally, a selection marker such as an antibiotic resistance gene.

The present invention further relates to an expression vector comprising said nucleic acid molecule and to a host cell transformed with said expression vector and expressing a BOD according to the invention.

The expression vector can be introduced into the host cell by any method known by a person skilled in the art, in particular, by modifying the membrane permeability of the host cell, for example in the presence of calcium ions, or by electroporation.

After culture of the host cells transformed for expressing the BOD according to the invention, said cells can be recovered by centrifugation, and lysed in order to release the enzymes, including said BOD according to the invention.

According to a preferred variant of the invention, the BOD according to the invention is produced by the yeast *Pichia pastoris*.

To permit overproduction and secretion of the BOD in the culture medium of the yeast *Pichia pastoris*, the nucleic acid molecule of SEQ. ID. No.4 coding for the BOD of sequence SEQ. ID. No.3 is introduced by homologous recombination in the yeast genome, at the level of the AOX1 gene. For this, the pFD55 plasmid, once linearized by digestion with the enzyme pmeI, is introduced into the yeast by electroporation and the positive clones are selected on YPD medium+agar containing zeocin at 100 μg/ml. A preculture of 200 mL of YPD medium supplemented with zeocin (100 μg/mL) is seeded with a clone isolated in a Petri dish. After stirring overnight at 220 rpm and at 30° C., this preculture is then centrifuged for 10 minutes at 4000 rpm and the pellet is taken up in 200 ml of sterile water to remove any glucose present. After a second centrifugation, a culture of 2 L in MMH medium containing 1 mM of $CuSO_4$ in a 5 L conical flask is then seeded with this pellet. The yeasts are incubated at 25° C. with stirring (220 rpm) for 2 hours before adding 0.5% of methanol to start induction. This induction step will be repeated for 5 days in order to obtain the maximum amount of enzymes.

For application of this method, it is possible, without any limiting character, to use the following materials:
  vector for expression in *Pichia pastoris* (pFD55): plasmid pPICZα containing the DNA sequence coding for the BOD from *Magnaporthe oryzae* in phase with the α-factor secretion factor of *Saccharomyces cerevisiae* and containing the methanol-inducible promoter AOX1.
  the yeast strain *Pichia pastoris* GS115 used for production of the BOD according to the invention after integration of the cassette derived from the pFD55 vector containing the promoter AOX1, the peptide signal α-factor and the DNA sequence coding for the BOD from *Magnaporthe oryzae*.
  Culture media:
Rich Medium YPD (for Yeast):
  1% yeast extract
  2% bacto-peptone
  2% glucose
  pH not adjusted, autoclaved for 20 min at 120° C.
Minimum Medium MMH (for Yeast):
  1.34% yeast nitrogen base
  1% Casamino acid
  0.4% histidine
  $4*10^{-5}$% biotin
  pH not adjusted, autoclaved for 20 min at 120° C.
Rich Medium LB (for Bacterium):
  Tryptone 10 g/L
  Yeast extract 5 g/L
  NaCl 5 g/L
  $H_2O$ distilled q.s. 1 L
  pH not adjusted, autoclaved for 20 min at 120° C.

According to another variant, *Escherichia coli* can be selected as the host microorganism, the plasmids that can then be used are notably the plasmids pBluescript, pUC18, pET, pGEX, pGS, pMAL-c2 or similar.

According to this variant of preparation of the BOD according to the invention, the BOD is advantageously expressed by an *E. coli* bacterium transformed with a pET21a expression vector coding for an enzyme fused to a 6HIS tag in C-terminal position.

This procedure is quick and simple; in fact, induction of expression of the BOD from *Magnaporthe oryzae* in the bacterium *E. coli* takes 4 to 24 hours.

Moreover, the 6HIS tag permits purification of the BOD from *Magnaporthe oryzae* by affinity chromatography on a nickel resin in a single step for obtaining a pure enzyme.

For application of this method of preparation, a person skilled in the art will select the host cell in relation to the expression vector used.

Preferably, when the pET21a expression vector is used, a host cell expressing T7 RNA polymerase will be selected, such as the *E. coli* strains $BL_{21}$ DE3, $BL_{21}$-SI, $BL_{21}$ pLys, Novablue (DE3) or $BL_{21}$ Star.

The present invention also relates to a method of preparing a BOD according to the invention comprising the steps of:
 a) preparing host cells expressing the BOD according to the invention;
 b) culturing the host cells prepared in step a);
 c) recovering the culture medium and removing the host cells, for example by centrifugation;
 d) treating the culture medium obtained in step c) by hydrophobic interaction chromatography;
 e) recovery of said purified BOD.

According to a preferred embodiment, the method according to the invention is such that:
 the strain of yeast *Pichia pastoris* used is strain GS115;
 the expression vector in *Pichia pastoris* (pFD55) is the plasmid pPICZα containing the DNA sequence coding for the BOD from *Magnaporthe oryzae* in phase with the secretion factor α-factor of *Saccharomyces cerevisiae* and containing the methanol-inducible promoter AOX1;
 the culture carried out in step b) comprises at least one step of liquid phase culture, with stirring, at a temperature between 18 and 37° C., preferably 25° C., during which the expression of the BOD is induced by adding methanol; induction by adding methanol can optionally be repeated.

When the method is applied according to these preferred conditions, it permits production of the BOD with a short induction time, of the order of 3 to 7 days; purification of the BOD is performed in a single step of hydrophobic interaction chromatography and the BOD thus produced certainly bears the four copper atoms necessary for its activity (see part 5 of the example).

When the BOD according to the invention is produced by a strain such as *Escherichia coli*, the method of preparing a BOD according to the invention comprises the steps of:
 a) preparing host cells expressing the BOD according to the invention;
 b) culturing the host cells prepared in step a);
 c) lysis of the host cells;
 d) treatment of the lysate obtained in step c) by affinity chromatography;
 e) recovery of said purified BOD.

It is also possible to produce a BOD in the presence of denaturing agents such as urea, guanidium chloride, SDS, triton etc.; the BOD thus produced will then be copper-free and can be activated by adding copper atoms.

The invention also relates to the use of the BOD from *Magnaporthe oryzae* according to the invention for determining bilirubin in solution, i.e. measuring the bilirubin concentration in a sample, notably a biological sample.

"Biological sample" means a biological fluid such as blood, serum, lymph, bile, urine, cerebrospinal fluid, sweat etc.

The presence of bilirubin in the body is normal, it arises from the degradation of haemoglobin and 200 to 230 mg of bilirubin is formed per day in a healthy adult. In someone in good health, bilirubin is captured by the liver and then degraded, therefore its concentration should not exceed certain thresholds and determination of bilirubin is useful for detecting disorders such as:
 cases of severe haemolysis: congenital or acquired haemolytic anaemias, drug-induced, toxic or infectious haemolysis, transfusion accident etc.;
 insufficient hepatic capture or conjugation: Gilbert disease, Crigler-Najjar disease, taking rifampicin (antituberculosis antibiotic);
 hepatic and biliary disorders: the various types of hepatitis (viral, toxic, drug-induced), the various types of cirrhosis, rare metabolic abnormalities (Rotor disease, Dubin-Johnson disease);
 biliary disorders;
 cholelithiasis;
 pancreatitides;
 cancer of the pancreas or of the biliary tract.

The present invention thus relates to the use of the BOD according to the present invention for measuring the bilirubin concentration in a fluid sample, in particular a biological sample.

According to a first variant, the principle of determining bilirubin with BOD is based on measurement of the colour change of the sample caused by the degradation of bilirubin.

Bilirubin has an absorption peak ($\lambda_{max}$) of light at 440 nm; when it is degraded enzymatically by a BOD, the absorbance at $\lambda_{max}$ of the sample in which it is present decreases; this decrease makes it possible to quantify the bilirubin initially present in the sample by comparison with the decrease in absorbance at 440 nm of standard solutions with known bilirubin contents measured in the same experimental conditions.

The present invention also relates to a kit for assay of bilirubin in solution, characterized in that it comprises a BOD according to the invention.

Typically, the assay kit also contains the reagents required for application of the bilirubin assay test, in particular:
 buffers;
 standard solutions of bilirubin for constructing calibration curves, and
 the instructions for use necessary for carrying out the assay.

The present invention further relates to a method for assay of bilirubin in solution in a fluid sample, characterized in that it comprises the following steps:
 a) measuring the absorbance at $\lambda_{max}$=440 nm of said fluid sample before enzymatic reaction;
 b) introducing a BOD according to the invention into said fluid sample;
 c) measuring the absorbance at $\lambda_{max}$=440 nm of said fluid sample after enzymatic reaction;
 d) calculating the difference in absorbance measured in steps a) and c) and comparing this difference with the differences in absorbances measured for standard solutions having a known bilirubin content;
 e) determining the initial bilirubin concentration of said fluid sample.

According to another variant, determination of the bilirubin in a fluid sample is performed by an electrochemical method employing an electrode including the BOD according to the invention.

Thus, the present invention also relates to BOD electrodes comprising a conducting material such as a conductive metal, notably platinum, copper, silver, aluminium, gold or steel or carbon, such as vitreous carbon, carbon fibres, fibres of carbon nanotubes or diamond etc., said conducting material is covered with a deposit comprising at least one BOD according to the invention; said deposit can moreover comprise a redox polymer for improving the electrical conduction between the enzyme and the electrode as well as the stability of the system.

The redox polymer can for example be selected from polymers based on ferrocene, osmium and ruthenium and conducting polymers, for example polypyrrole and polyaniline.

The methods of immobilizing the BOD on said conducting material can be selected from the conventional methods available to a person skilled in the art, which notably comprise inclusion of the BOD in a polymer matrix, adsorption of the BOD on the surface of the polymer membrane, fixation by covalent bond, electrodeposition (Gao et al., Chem. Int. ED. 2002, 41, No. 5, 810-813) or the technique described in American patent application US 2009/0053582.

According to one embodiment, the BOD electrode on which the BOD is immobilized is also covered with a membrane that prevents detachment of said enzyme from the electrode. Depending on the applications envisaged, said membrane can consist of Nafion, cellulose or any biocompatible material, i.e. compatible with a physiological environment.

The present invention thus also relates to a bilirubin biosensor consisting of a BOD electrode according to the invention. In general, a biosensor consists of an electrode on which a bioreceptor capable of recognizing a biological target is immobilized; fixation of the biological target on the bioreceptor leads to physicochemical changes of the membrane and the production of an electrical signal by an electrochemical transducer (amperometric, potentiometric, conductometric, etc.) fused to the electrode. In the present case, the bioreceptor is a BOD according to the invention and the biological target is bilirubin.

The present invention further relates to a method for assay of bilirubin in solution in a fluid sample with a bilirubin biosensor according to the invention.

According to a variant of use of the bilirubin biosensor, the latter is implanted under a person's skin and makes it possible to record the bilirubin concentration in the blood of said person.

The present invention also relates to an oxygen sensor consisting of an electrode according to the invention.

The BOD electrode according to the invention can moreover be used advantageously as the cathode in an enzymatic biofuel cell; FIG. 1A shows schematically the operating principle of an enzymatic biofuel cell. The enzymatic biofuel cells according to the invention are devices comprising a BOD electrode as cathode and an anode where a reaction of oxidation of a substrate takes place (catalysed by "enzyme X"); as an illustration, the substrate can be glucose and "enzyme X" glucose oxidase; a fuel cell of this kind is of particular interest when the biofuel cell is implanted in an individual for a medical application; the substrate can also be selected, for example, from nitrites, nitrates, sulphides, urates, ascorbates, glutamates, pyruvates, lactates, cellulose, etc. If a decontamination application is envisaged, the enzyme will then be selected in relation to the substrate to be degraded, as an example, the following enzymes can be used, with the type of substrate that they can degrade shown in parentheses: glucose oxidase (glucose or all sugars that are oxidized by this enzyme), lactate oxidase (lactate), pyruvate oxidase (pyruvate), alcohol oxidase (alcohol), cholesterol oxidase (cholesterol), glutamate oxidase (glutamate), pyranose oxidase (pyranose), choline oxidase (choline), cellobiose dehydrogenase (cellobiose), glucose dehydrogenase (glucose or all sugars that are oxidized by this enzyme), pyranose dehydrogenase (pyranose), fructose dehydrogenase (fructose), aldehyde oxidase (aldehyde), gluconolactone oxidase (gluconolactone), alcohol dehydrogenase (alcohol), ascorbate oxidase (oxygen or ascorbate) or sulphide dioxygenase (sulphide). The process of oxidation and concomitant reduction at the electrodes of the biofuel cell produces an electric current.

FIG. 1B illustrates more specifically an enzymatic biofuel cell with glucose; this enzymatic biofuel cell consists of two electrodes modified by immobilization of enzymes. A glucose oxidase (GOx) is fixed on the anode (1) via a conducting polymer "I" and a bilirubin oxidase (BOD) is fixed on the cathode (2) via a conducting polymer "II". In operation, at the anode, the electrons are transferred from the glucose present in the physiological fluid to the GOx, then from the GOx to the conducting polymer "I" and from the conducting polymer "I" to the anode. At the cathode, the electrons are transferred from the cathode to the conducting polymer "II", then to the BOD and finally from the BOD to the oxygen present in the physiological fluid.

It should be noted that a biofuel cell can also optionally function by modifying the electrodes with their respective enzymes and adding soluble mediators, such as ferrocenemethanol for the anode and potassium ferricyanide for the cathode, and if necessary adding a membrane separating the anode and cathode.

The present invention further relates to a method of assaying glycated haemoglobin using a BOD electrode as described above as cathode and comprising the following steps:
a) measuring the free oxygen in a standard buffer solution;
b) measuring the free oxygen in a blood sample;
c) comparing the measurements performed in steps a) and b) and deduction of a haemoglobin content in the blood sample;
d) extraction of the glycated haemoglobin from said blood sample;
e) measuring the free oxygen in a blood sample obtained in step d);
f) comparing the measurements performed in steps b) and c) and deduction of a content of glycated haemoglobin in said blood sample.

Alternatively, the measurement in step e) can be performed directly on the glycated haemoglobin extracted from the blood sample. The variants of application of this method are described in application US 2002/017992.

According to another aspect, the present invention relates to the use of a BOD according to the invention for degrading the bilirubin present in a sample, notably a biological sample. In fact, the presence of bilirubin in a sample may falsify the detection of other substances (such as glucose or blood cholesterol) especially when these other substances are detected by a colorimetric method.

In general, the BODs according to the invention find numerous industrial applications, notably in the textile and papermaking industries and in the food industry, for example to improve the stability and/or quality of foodstuffs, such as drinks, or of foodstuffs containing vegetable oils by deoxygenation.

More specifically, the BODs can be used for applications connected with decontamination, and for example we may mention wastewater decoloration and/or detoxification and the degradation of xenobiotics; as organic synthesis reagents; for preparing antimicrobial compositions; for the manufacture of articles in wood and of detoxified cardboards or for detergent manufacture (Morozova et al. Biochemistry (Mosc.) 2007 October; 72(10):1136-50) and for bleaching of dyes used in industrial media; in particular for bleaching textiles and for bleaching paper pulp.

The BOD according to the invention can also be used for dimerizing phenolic acid (Koschorreck, K., et al. 2008. Appl Microbiol Biotechnol (2008) 79:217-224) and is thus of interest for the synthesis of pigments and dyes used in textile and food applications (R. Mustafa et al. Food Research International. Volume 38, Issues 8-9, October-November 2005, Pages 995-1000); this dimerization reaction can also be used for preparing antioxidants, for example, dimers of ferulic acid (Garcia-Conesa M T, et al. Redox Rep. 1997 October-December; 3(5-6):319-23).

The BOD according to the invention can also be used as reagent in a composition for oxidation dyeing of keratin fibres, such as a composition for colouring the hair, comprising, in a suitable medium for dyeing, at least one oxidation base, a BOD according to the invention and, optionally, a donor for said BOD (for instance a substrate such as bilirubin). The various ingredients, other than the BOD, usable in said composition are described in international application WO 99/15138; as an example, the oxidation base or bases can be selected from paraphenylenediamines, double bases, paraminophenols, orthoaminophenols and heterocyclic oxidation bases.

The BOD according to the invention can advantageously be used for treatment of paper pulp for bleaching the pulp and/or for its action on lignin degradation (delignification) and/or to produce paper that has better moisture resistance (see international application WO 00/68500).

Besides the foregoing provisions, the invention further comprises other provisions which will become clear from the description given below, relating to examples of application of the present invention, as well as the appended figures in which:

FIGURES

EXAMPLE

1. Materials
1.1 Bacterial Strain of *Escherichia coli*

$DH_5\alpha$: supE44, ΔlacU169, (Φ80 lacZDM15), hsdR17, recA1, endA1, gyrA96, thi-1, relA1 (Hanahan, 1983).

This strain is used for amplification of plasmids in the steps of construction of the protein expression vectors.

1.2 Vector pFD55: Plasmid pPICZα containing the DNA sequence of SEQ. ID No. 2 coding for the BOD from *Magnaporthe oryzae* in phase with the α-factor secretion factor of *Saccharomyces cerevisiae* and containing the methanol-inducible promoter AOX1.

Figure 1A:
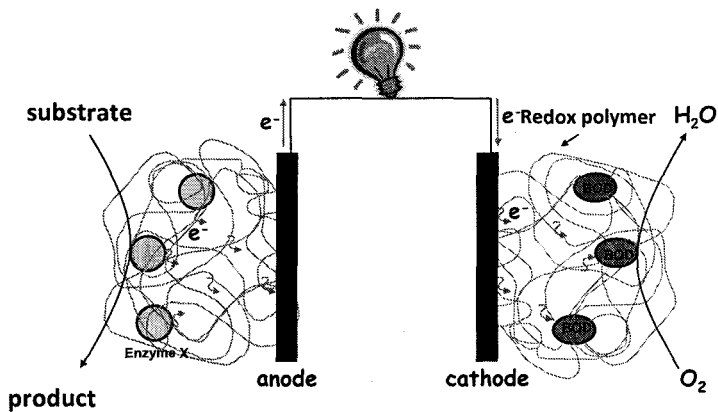
FIG. 1A shows schematically the operating principle of an enzymatic biofuel cell.
Figure 1B:
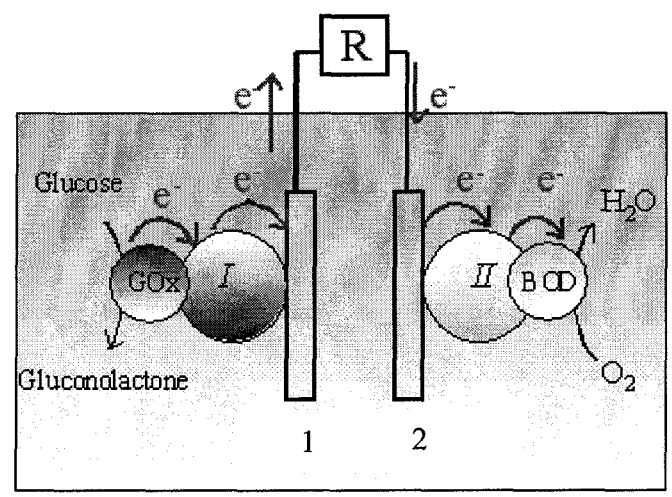
FIG. 1B shows a glucose-based enzymatic biofuel cell.
Figure 2:
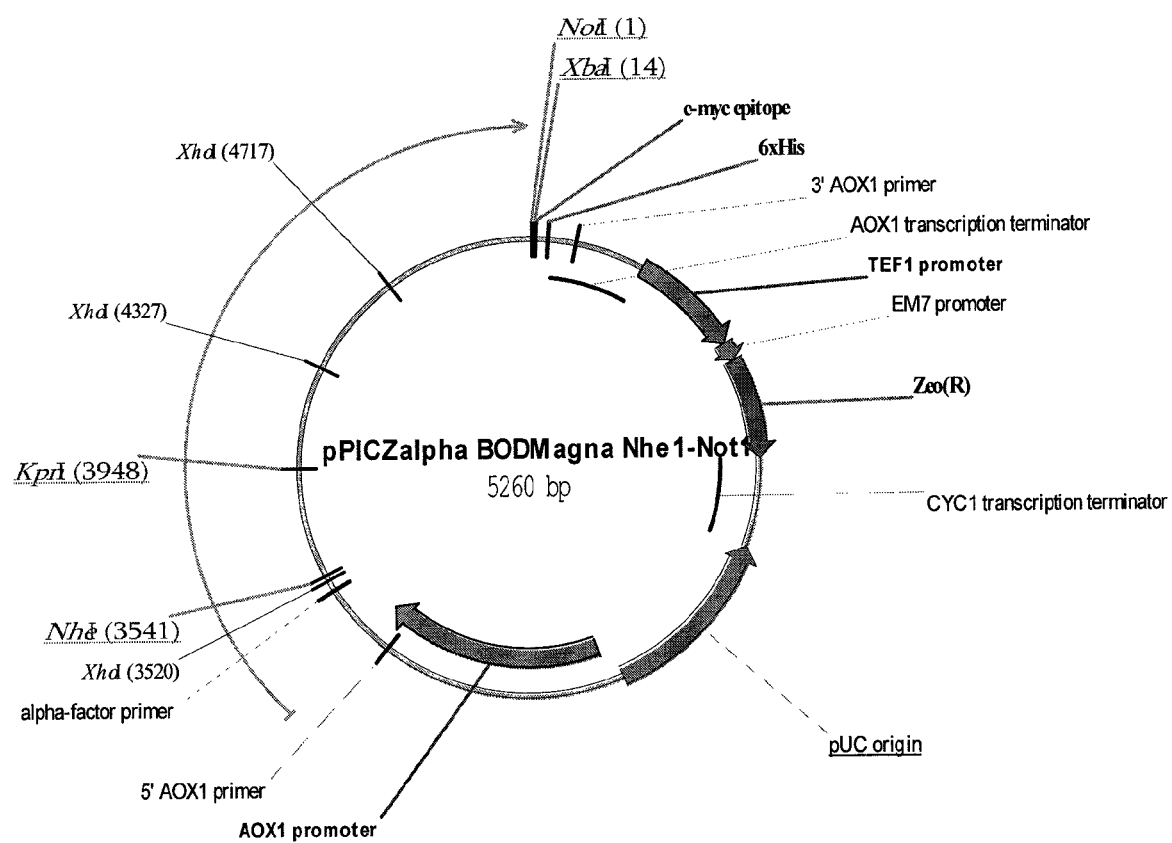
FIG. 2 shows the plasmid map of the pFD55 vector.

The plasmid map of the pPICZα plasmid is shown in FIG. 2.

1.3 Strain of the Yeast *Pichia pastoris*

GS115: *Pichia pastoris* yeast strain used for production of bilirubin oxidase after integration of the cassette derived from the pFD55 vector containing the AOX1 promoter, the α-factor secretion factor and the DNA sequence coding for the BOD from *Magnaporthe oryzae*.

1.4 Culture Media
Rich Medium YPD (for Yeast):
1% yeast extract
2% bacto-peptone
2% glucose
pH not adjusted, autoclaved for 20 min at 120° C.
Minimum Medium MMH (for Yeast):
1.34% yeast nitrogen base
1% Casamino acid
0.4% histidine
$4*10^{-5}$% biotin
pH not adjusted, autoclaved for 20 min at 120° C.
Rich Medium LB (for Bacterium):
Tryptone 10 g/L
Yeast extract 5 g/L
NaCl 5 g/L
$H_2O$ distilled q.s. 1 L
pH not adjusted, autoclaved for 20 min at 120° C.

2. Genetic Engineering Techniques
2.1 Transformation of the Supercompetent Bacteria The $DH_{5\alpha}$ supercompetent bacteria are prepared by the SEM method (Simple and Efficient Method) according to the protocol described by Inoue et al. (Inoue et al. 1990. Gene 96:23-28).

2.2 Transformation of the Yeast *Pichia pastoris*

The DNA is introduced into the yeast *Pichia pastoris* GS115 by electroporation on an Eppendorf Eporator (Eppendorf, France).

2.3 Preparation of the DNA

A plasmid DNA purification kit (Quiagen) is used for the DNA preparations in small and large amount.

2.4 Sequencing of the Double-Stranded DNA

The double-stranded DNA is sequenced by the company Millegen (Toulouse, France) according to conventional techniques.

2.5 Construction of Expression Vector of BOD

The gene corresponding to the sequence coding for the bilirubin oxidase of *Magnaporthe oryzae* (accession number A4QV27) cleaved at the level of the first 24 amino acids positioned at the N-terminal end of the protein was synthesized by the company Genecust Europe (Luxembourg). The restriction sites NheI (SEQ. ID. No.6: gctagc) and NotI (SEQ. ID. No.7: gcggccgc), respectively, were added at 3' and 5' of the sequence to facilitate cloning.

The pPICZα plasmid as well as the synthesized gene were then treated with the two restriction enzymes NheI and NotI and the digestion products were purified on gel with the "nucleospin" kit.

The gene of the BOD is then ligated into the plasmid by co-incubation with T4 DNA Ligase at 37° C. overnight.

The neoformed plasmids (pFD55) are then selected and amplified by transformation of DH5α bacteria in a dish containing zeocin at 25 µg/ml.

2.6 Integration of the Sequence Coding for Bilirubin Oxidase in the Genome of *Pichia pastoris*

To permit overproduction and secretion of the enzyme in the culture medium of the yeast *Pichia pastoris*, the corresponding gene is introduced by homologous recombination at the level of the AOX1 gene. For this, the pFD55 plasmid, once linearized by digestion with the enzyme pmeI, is introduced into the yeast by electroporation and the positive clones are selected on YPD medium+agar containing zeocin at 100 µg/ml.

3. Production, Purification and Characterization of the BOD from *Magnaporthe oryzae*

3.1 Production of BOD

The enzyme BOD is produced by the yeast *Pichia pastoris* via methanol induction. For this purpose, a preculture of 200 mL of YPD medium supplemented with zeocin (100 µg/mL) is seeded with GS115 strain after integrating the cassette contained on the pFD55 plasmid. After stirring overnight at 220 rpm at 30° C., this preculture is then centrifuged for 10 minutes at 4000 rpm and the pellet is taken up in 200 ml of sterile water to remove any glucose present. After a second centrifugation, a culture of 2 L in MMH medium containing 1 mM of $CuSO_4$ in a 5 L conical flask is then seeded with this pellet. The yeasts are incubated at 25° C. with stirring (220 rpm) for 2 hours before adding 0.5% of methanol to start induction. This induction step will be repeated for 5 days in order to obtain a maximum amount of enzymes. To recover the secreted proteins, the 2 L culture is centrifuged and the supernatant containing the enzyme of interest is concentrated in a shaking cell with a YM10 membrane with a cut-off of 10 kDa to achieve a final volume of 4-5 ml.

3.2 Purification of BOD by Hydrophobic Interaction Chromatography

Once concentrated, 1.7 M of ammonium sulphate is added to 4-5 ml of the culture supernatant before it is filtered on a 0.22 µm filter for injection on a hydrophobic interaction column, a 60 ml PhenylHP (GE Healthcare®), coupled to the system AKTA purifier (GE Healthcare®), equilibrated in 50 mM potassium phosphate buffer, $(NH_4)_2SO_4$ 1.7 M, pH 6. Elution is carried out with a gradient from 0% to 100% of a 50 mM potassium phosphate buffer pH 6 at a flow rate of 2.5 mL/min. The fractions containing the BOD protein are identified by an ABTS activity test (2,2'-azino-bis(3-ethylbenzothiazoline-6-sulphonic acid) and are combined, concentrated and stored in 50 mM potassium phosphate buffer pH 6 by centrifugation on Amicon YM10 membrane. At this stage, the BOD protein is pure and can be stored at –20° C. in soluble form. On comparing with the other available commercially BODs, it should be emphasized that there is a real advantage in using this protein with respect to the purification protocol. In fact, a single purification step is required for obtaining a pure enzyme, in contrast to the successive steps of chromatography (size exclusion, anion- or cation-exchange, hydrophobic, etc.) used for the other known bilirubin oxidases.

3.3 Characterization of the Enzyme

3.3.1 Measurement of Concentration

The concentration of enzyme in a solution is calculated from a BSA range according to Bradford's technique (Bradford, M. M., *A rapid and sensitive method for the quantitation of microgram quantities of protein utilizing the principle of protein-dye binding*. Anal Biochem, 1976. 72: p. 248-54).

3.3.2 Enzyme Tests

The enzyme tests are carried out using a Varian spectrophotometer in 0.1M citrate/phosphate buffer at 37° C. in a volume of 3 mL, monitoring the oxidation of different substrates at a given wavelength as a function of time. The specific activity of the enzyme is expressed in µmoles of substrates oxidized per minute and per mg of protein. The substrates used in this study are: ABTS ($\epsilon_{420\,nm}$=36 $mM^{-1}$ $cm^{-1}$), unconjugated bilirubin ($\epsilon_{450\,nm}$=32 $mM^{-1}$ $cm^{-1}$) and conjugated bilirubin ($\epsilon_{440\,nm}$=25 $mM^{-1}$ $cm^{1}$).

3.4 Investigation of the Enzymatic Properties of the BOD from *Magnaporthe oryzae*

3.4.1 Determination of the Kinetic Constant ($k_{cat}$) and Michaelis Constant ($K_M$) in the Steady State

3.4.1.1 ABTS

The experiments are conducted at 37° C. on a Varian spectrophotometer in 0.1M citrate/phosphate buffer pH 4. The ABTS concentration varies in the assay from 0 to 4 mM. The assay is started by adding enzyme. The test points are analysed by non-linear regression according to the Michaelis-Menten model using the Sigma-plot 6.0 software according to the equation: $k_{ss}=k_{cat}*[S]/(K_M+[S])$ Results:

$k_{cat}$=664 s−1 and $K_m$=428 µM

Figure 3:
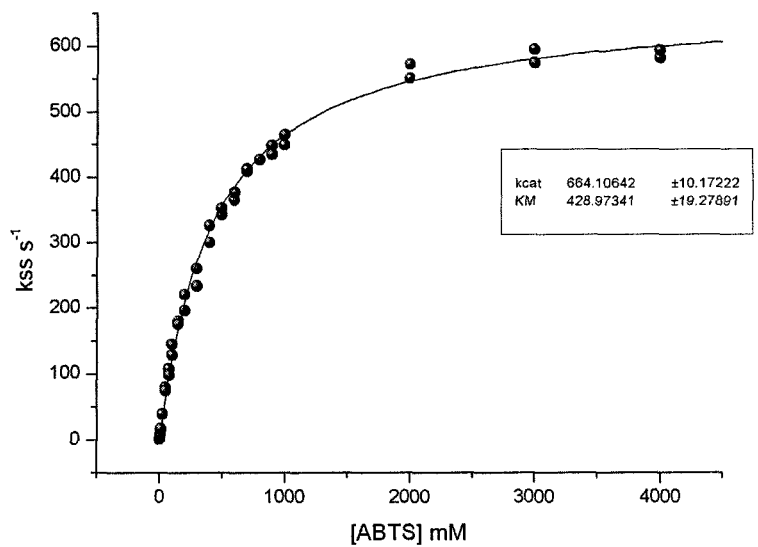
FIG. 3 shows the catalytic activity of the BOD from *Magnaporthe oryzae* as a function of the ABTS concentration.

The catalytic activity of the BOD from *Magnaporthe oryzae* as a function of the ABTS concentration is shown in FIG. 3.

For comparison, the BOD from *Myrothecium verrucaria* produced in *Pichia pastoris* shows, with respect to ABTS at pH 6.5, a $k_{cat}$ of 164 $s^{-1}$ for a $K_m$ of 340 µM (Bradford, M. M., *A rapid and sensitive method for the quantitation of microgram quantities of protein utilizing the principle of protein-dye binding*. Anal Biochem, 1976. 72: p. 248-54).

3.4.1.2 Unconjugated Bilirubin

Figure 4:
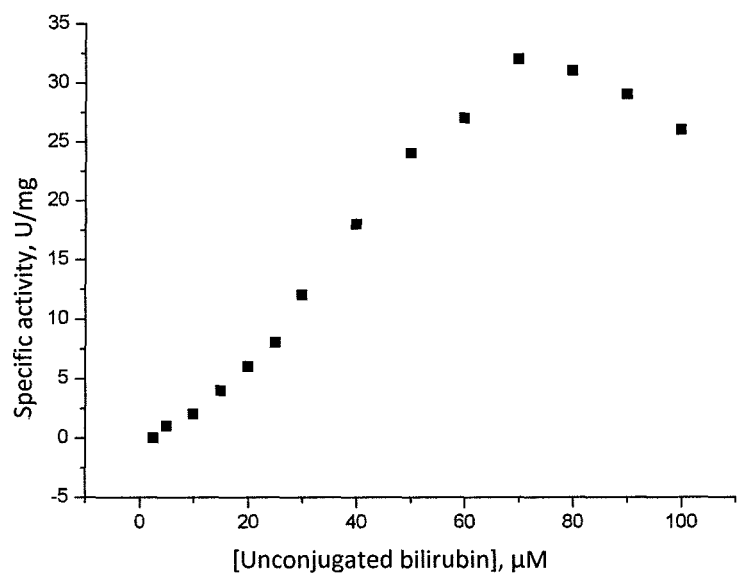
FIG. 4 shows the catalytic activity of the BOD from *Magnaporthe oryzae* as a function of the concentration of unconjugated bilirubin.

The experiments are conducted at 37° C. on a Varian spectrophotometer in a Tris-HCl 50 mM buffer pH 8.5. The concentration of bilirubin varies in the assay from 0 to 100 µM. The assay, started by adding enzyme, consists of monitoring the oxidation of unconjugated bilirubin at 450 nm from the colorimetric variation ($\epsilon_{450\,nm}$=32 $mM^{-1}.cm^{-1}$). As shown in FIG. 4, the oxidation of this substrate does not follow a Michaelis-Menten process and therefore it is not possible to determine the usual constants.

Only the value of the maximum specific activity can be given, with a calculated value of 32 U/mg.

For comparison, the BODs derived from the fungus *Myrothecium verrucaria* and from the bacterium *Bacillus subtilis* display a maximum specific activity of 24 U/mg and 28 U/mg respectively for this same substrate (Kataoka, K., et al., *High-level expression of Myrothecium verrucaria bilirubin oxidase in Pichia pastoris, and its facile purification and characterization*. Protein Expr Purif, 2005. 41(1): p. 77-83 and Sakasegawa, S., et al., Bilirubin oxidase activity of *Bacillus subtilis* CotA. Appl Environ Microbiol, 2006. 72(1): p. 972-5.ù).

3.4.1.3 Conjugated Bilirubin

The experiments are conducted at 37° C. on a Varian spectrophotometer in a citrate-phosphate buffer 50 mM pH 3.6. The bilirubin concentration varies in the assay from 0 to 100 µM. The assay, started by adding enzyme, consists of monitoring the oxidation of conjugated bilirubin at 440 nm based on colorimetric variation ($\epsilon_{440\,nm}$=25 $mM^{-1}$ $cm^{-1}$). The test points are analysed by non-linear regression according to the Michaelis-Menten model using the Sigma-plot 6.0 software according to the following equation:

$$k_{ss}=k_{cat}*[S](K_M+[S])$$

This enzyme thus has the following kinetic constants with respect to conjugated bilirubin: $k_{cat}$=28 $s^{-1}$ and $K_M$=18.5 µM.

Figure 5:
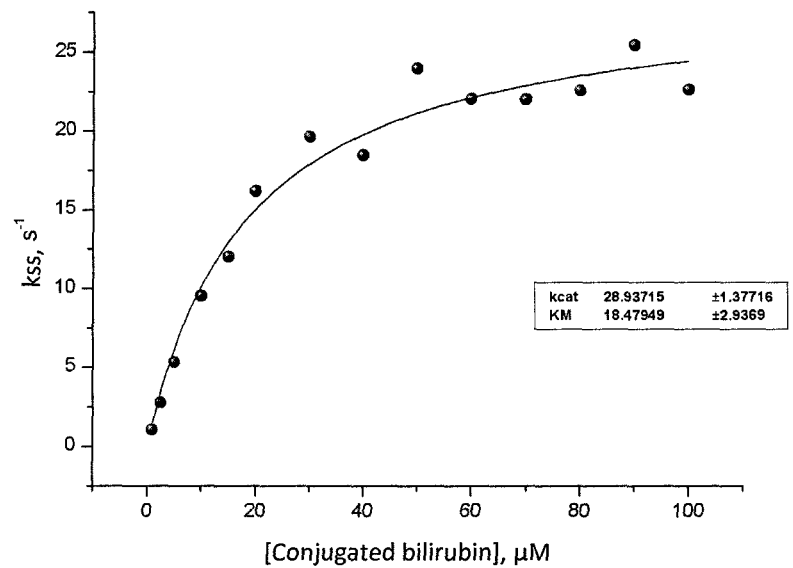
FIG. 5 shows the catalytic activity of the BOD from *Magnaporthe oryzae* as a function of the concentration of conjugated bilirubin.

The catalytic activity of the BOD from *Magnaporthe oryzae* as a function of the concentration of conjugated bilirubin is shown in FIG. 5.

3.4.2 Investigation of Enzymatic Activity as a Function of pH 3.4.2.1 ABTS

The variation in reaction rate constant as a function of pH is investigated over a pH range from 3 to 7 in 0.1M citrate/phosphate buffer using ABTS at 1 mM as substrate. The experiments are conducted at 37° C. using a Varian spectrophotometer. The activity is monitored from the oxidation of ABTS leading to a colorimetric variation measured at 420 nm. The assay is started by adding enzyme.

3.4.2.2 Unconjugated Bilirubin

The variation in reaction rate constant as a function of pH is investigated over a pH range from 7 to 8.5 in a Tris-HCl 0.2M buffer using unconjugated bilirubin at 30 μM as substrate. The experiments are conducted at 37° C. using a Varian spectrophotometer. The activity is monitored from the oxidation of bilirubin, leading to a colorimetric variation measured at 450 nm ($\epsilon_{450\ nm}$=32 $mM^{-1}$ $cm^{-1}$). The assay is started by adding enzyme.

3.4.2.3 Conjugated Bilirubin

Figure 6:
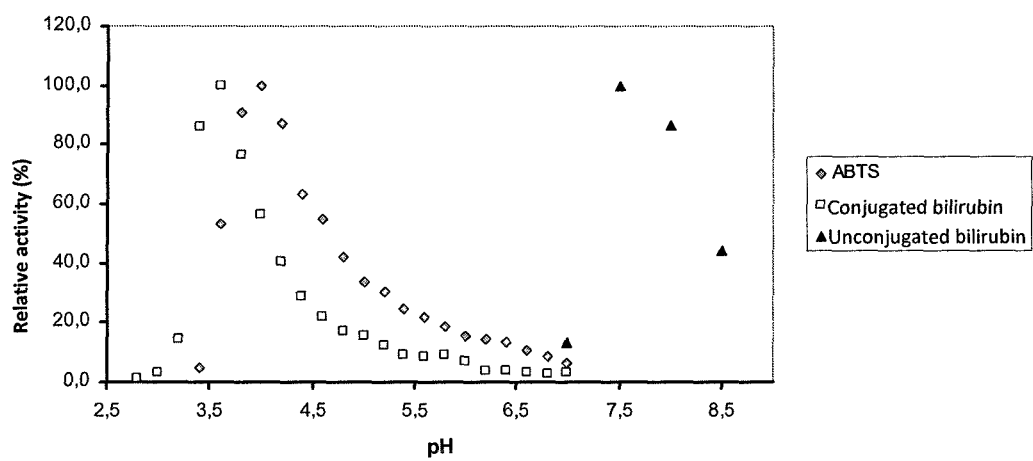
FIG. 6 shows the relative activity of the BOD from *Magnaporthe oryzae* as a function of pH on the oxidation of different substrates.

The variation in reaction rate constant as a function of pH is investigated over a pH range from 3 to 7 in a 0.1 M citrate/phosphate buffer using conjugated bilirubin at 25 μM as substrate. The experiments are conducted at 37° C. using a Varian spectrophotometer. The activity is monitored from the oxidation of bilirubin, leading to a colorimetric variation measured at 440 nm ($\epsilon_{450\ nm}$=25 $mM^{-1}$ $cm^{-1}$). The assay is started by adding enzyme. The relative activity of the BOD from *Magnaporthe oryzae* as a function of pH on the oxidation of different substrates is shown in graph form in FIG. 6.

3.4.3 Investigation of Enzymatic Activity as a Function of Temperature

Figure 7:
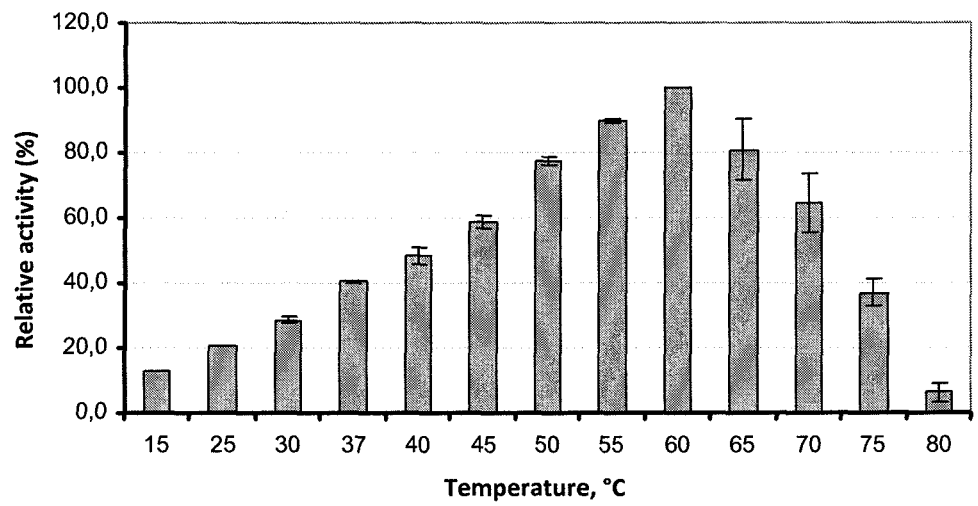
FIG. 7 shows the test of activity of the BOD from *Magnaporthe oryzae* as a function of temperature on the oxidation of ABTS.

The variation in reaction rate constant as a function of temperature is investigated in a 0.1 M citrate/phosphate buffer pH 4 in the presence of 0.5 mM of ABTS. The temperature varies from 15 to 80° C. The activity is monitored on a temperature-controlled Varian spectrophotometer CARY UV Biomelt. The assay is started by adding enzyme. The results of oxidation of ABTS as a function of temperature by the BOD from *Magnaporthe oryzae* are shown as relative activity on the graph in FIG. 7.

3.4.4 Stability of the Enzyme as a Function of Temperature

The enzyme is preincubated at a concentration of 0.15 mg/ml in a dry bath at 60° C. and at 37° C. in 50 mM potassium phosphate buffer pH 6. At regular intervals, 5 μL samples are collected and the residual activity of the enzyme incubated at these temperatures is determined using a Varian spectrophotometer at 440 nm in 0.1M citrate/phosphate buffer pH 3.8 at 37° C., in the presence of 50 μM of conjugated bilirubin. The assay is started by adding enzyme.

Figure 8:
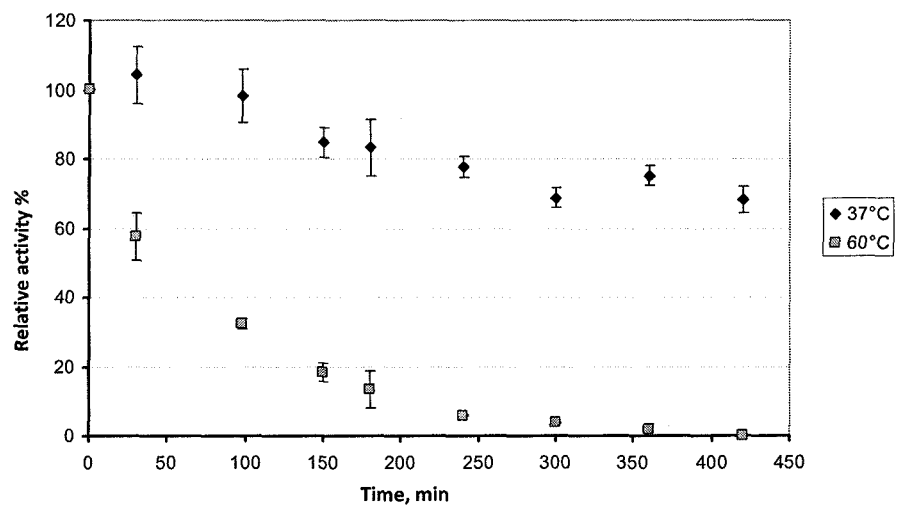
FIG. 8 shows the test of stability of the BOD from *Magnaporthe oryzae* as a function of temperature on the oxidation of conjugated bilirubin.

The results of oxidation of conjugated bilirubin as a function of temperature by the BOD from *Magnaporthe oryzae* are shown as relative activity on the graph in FIG. 8.

3.4.5 Activity of Bleaching Remazol Brilliant Blue R

The effectiveness of bleaching Remazol Brilliant Blue R(RBBR) by the BOD from *Magnaporthe oryzae* was measured in a phosphate-citrate buffer 50 mM pH 7 in the presence or absence of ABTS at 10 μM. A solution of RBBR at 80 mg/L is preincubated at 37° C. with or without ABTS and the enzyme is added at TO at a concentration of 10 μg/ml. The absorbance at 592 nm (absorption peak of RBBR) is measured at regular intervals to monitor the bleaching activity of the enzyme.

After just 20 minutes, more than 94% of RBBR is bleached in the presence of ABTS 10 μM at 37° C. This result clearly demonstrates the excellent potential of this enzyme for bleaching dyes used in the textile industry for example.

Figure 9:
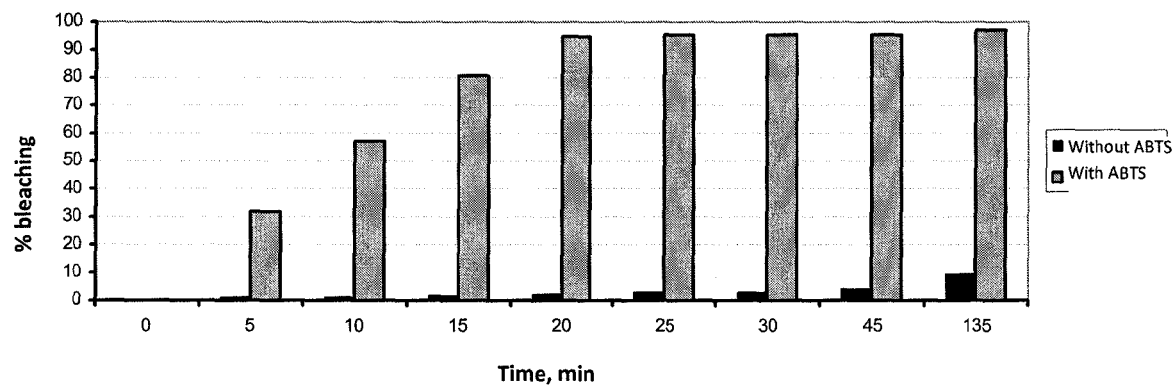
FIG. 9 shows the percentage bleaching of Remazol Brilliant Blue R by the BOD from *Magnaporthe oryzae* at 37° C. in a phosphate-citrate buffer 50 mM pH 7.
Figure 10:
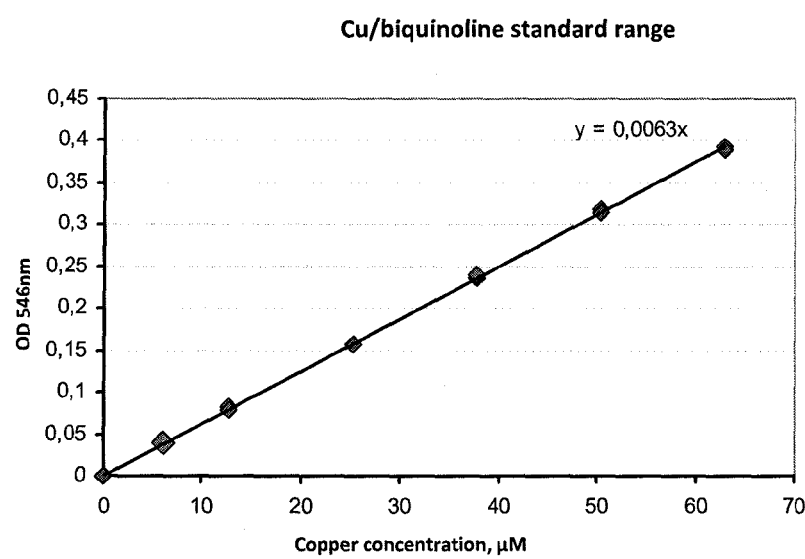
FIG. 10 shows the calibration curve for measurement of copper via the biquinoline test.

FIG. 9 shows the percentage bleaching of Remazol Brilliant Blue R by the BOD from *Magnaporthe oryzae* at 37° C. in a phosphate-citrate buffer 50 mM pH 7.

3.5 Determination of the Four Coppers for the BOD of *Magnaporthe oryzae* Produced in *Pichia pastoris*

The presence of the 4 coppers is determined by a biquinoline assay using a standard range for measuring the molar concentration of copper (Table 1) (Felsenfeld, G., *The determination of cuprous ion in copper proteins*. Arch Biochem Biophys, 1960. 87: p. 247-5).

TABLE 1

Experimental protocol for the biquinoline assay required for determination of copper in BOD.

| sample | Copper solution (solution 2) (μL) | Imidazole buffer (solution 1) (μL) | Biquinoline (solution 3) (μL) | Total volume (μL) | Copper concentration in sample (μM) |
|---|---|---|---|---|---|
| 1 | 0 | 1200 | 1800 | 3000 | 0 |
| 2 | 0 | 1200 | 1800 | 3000 | 0 |
| 3 | 120 | 1080 | 1800 | 3000 | 12.59 |
| 4 | 120 | 1080 | 1800 | 3000 | 12.59 |
| 5 | 240 | 960 | 1800 | 3000 | 25.18 |
| 6 | 240 | 960 | 1800 | 3000 | 25.18 |
| 7 | 360 | 840 | 1800 | 3000 | 37.77 |
| 8 | 360 | 840 | 1800 | 3000 | 37.77 |
| 9 | 480 | 720 | 1800 | 3000 | 50.36 |
| 10 | 480 | 720 | 1800 | 3000 | 50.36 |
| 11 | 600 | 600 | 1800 | 3000 | 62.95 |
| 12 | 600 | 600 | 1800 | 3000 | 62.95 |
| BOD_1 (1.5 μm) | 450 | 750 | 1800 | 3000 | 6.1 |
| BOD_2 (1.55 μm) | 450 | 750 | 1800 | 3000 | 6.3 |

Each measurement, based on a colorimetric assay at 546 nm, is performed in duplicate. FIG. 10 shows the calibration curve for measurement of copper by the biquinoline assay. This technique made it possible to demonstrate the presence of 6.1 μM of copper for a protein sample of BOD of 1.5 μM i.e. a ratio of 4.06 and is good confirmation of the presence of the four copper ions associated with the enzyme.

The invention claimed is:

1. A purified bilirubin oxidase (BOD) electrode comprising a conducting material covered with a deposit comprising at least one BOD, said BOD having a percentage identity of at least 90% relative to the BOD from *Magnaporthe oryzae* of SEQ ID NO: 1, and wherein the addition, substitution, deletion or insertion of amino acids are within the N-terminal end; wherein said BOD catalyses the oxidation reaction of bilirubin to biliverdin; and wherein said BOD is bound to four copper atoms.

2. A bilirubin biosensor, wherein said biosensor consists of an electrode according to claim 1.

3. An oxygen sensor, wherein said sensor consists of an electrode according to claim 1.

4. An enzymatic biofuel cell comprising an anode on which an enzyme catalyzing a reaction of oxidation is immobilized and an electrode according to claim 1 as cathode.

5. Method of assaying glycated haemoglobin using an oxygen sensor according to claim 3 comprising the following steps:
   a) measuring the free oxygen in a standard buffer solution;
   b) measuring the free oxygen in a blood sample;
   c) comparing the measurements performed in steps a) and b) and deduction of a haemoglobin content in the blood sample;
   d) extraction of the glycated haemoglobin from said blood sample;
   e) measuring the free oxygen in a blood sample obtained in step d);
   f) comparing the measurements performed in steps b) and c) and deduction of a content of glycated haemoglobin in said blood sample.

\* \* \* \* \*